United States Patent [19]

Bach et al.

[11] Patent Number: 4,801,754
[45] Date of Patent: Jan. 31, 1989

[54] HYDROFORMYLATION PROCESS

[75] Inventors: Hanswilhelm Bach, Duisburg; Boy Cornils, Hofheim; Wilhelm Gick, Duisburg; Gehard Diekhaus, Oberhausen; Werner Konkol, Oberhausen; Ernest Wiebus, Oberhausen, all of Fed. Rep. of Germany

[73] Assignee: Ruhrchemie Aktiengesellschaft, Fed. Rep. of Germany

[21] Appl. No.: 125,595

[22] Filed: Nov. 25, 1987

[30] Foreign Application Priority Data

Nov. 27, 1986 [DE] Fed. Rep. of Germany ....... 3640615

[51] Int. Cl.$^4$ .............................................. C07C 45/50
[52] U.S. Cl. ..................................... 568/454; 568/451
[58] Field of Search ................................ 568/454, 492

[56] References Cited

U.S. PATENT DOCUMENTS 4,547,595 10/1985 Chang ................................. 568/454

FOREIGN PATENT DOCUMENTS 0096987 12/1983 European Pat. Off. ............ 568/456
2627354 4/1980 Fed. Rep. of Germany ...... 568/454
3017651 11/1980 Fed. Rep. of Germany ...... 568/454
3338340 5/1984 Fed. Rep. of Germany .
3341035 5/1985 Fed. Rep. of Germany ...... 568/454
0216315 9/1985 Fed. Rep. of Germany ...... 568/454
3511428 10/1986 Fed. Rep. of Germany ...... 568/454

*Primary Examiner*—Werren B. Lone
*Attorney, Agent, or Firm*—Bierman and Muserlian

[57] ABSTRACT

In a hydroformylation process for the preparation of aldehydes by reacting aliphatic olefins of 2 to 12 carbon atoms with carbon monoxide and hydrogen at temperatures of 20° to 150° C. and pressures of 0.1 to 20 mPa in the liquid phase and in the presence of an aqueous solution containing 50 to 800 wt. ppm of rhodium and 25 to 30 wt. % of phosphines, in each case based on the aqueous solution as a catalyst system and in addition the transformation products of the phosphines, the improvement comprising draining off a portion of the aqueous solution of the catalyst system together with the reaction product and replacing the same by fresh aqueous solution of the catalyst system whereby the original catalyst selectivity for formation of n-aldehydes is maintained.

2 Claims, No Drawings

HYDROFORMYLATION PROCESS

STATE OF THE ART

DE No. 2,627,354 C3 describes a hydroformylation process in which olefin, carbon monoxide and hydrogen are reacted in the liquid phase in the presence of water and rhodium complex compounds and solubility of the catalytically active rhodium complex compounds is attained by the use of sulfonated triarylphosphines as a complexing component. This procedure has a number of remarkable advantages. In particular, it permits very simple separation of the reaction product and the catalyst and ensures near-complete recovery of the rhodium. The catalyst is separated from the reaction product simply by separation of the organic and aqueous phases, i.e. without distillation and thus without additional thermal loading of the aldehydes and alcohols formed. Due to the extremely low solubility of the catalyst in the aldehyde and alcohol, hardly any precious metal is removed with the reaction product, either. Finally, poisoning of the catalyst by high-boiling by-products formed, for example, by aldolization or aldol condensation or acetal formation is largely avoided.

The rhodium complex compounds used as catalyst contain a maximum of three phosphine molecules per rhodium atom and they correspond to the formula $HRh(CO)_xL_{4-x}$, where L denotes the water-soluble phosphine ligand and x is a number from 1 to 3. To increase the stability of the rhodium complex compounds, they are used in the form of a catalyst system which has a high phosphine excess in relation to the rhodium present. Normally, 10 to 300 gram molecules, preferably 50 to 150 gram molecules, of water-soluble phosphine are added per 1 g-atom of rhodium.

The water-soluble phosphine ligands have the formula

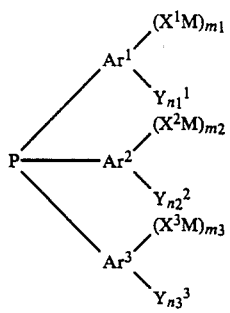

In this formula $Ar^1$, $Ar^2$, $Ar^3$ individually are phenyl or naphthyl, $Y^1$, $Y^2$, $Y^3$ individually are a straight-chain or branched alkyl or alkoxy of 1 to 4 carbon atoms, halogen, OH, CN, $NO_2$ or $R^1R^2N$ where $R^1$ and $R^2$ individually are straight-chain or branched alkyl of 1 to 4 carbon atoms; $X^1$, $X^2$, $X^3$ individually are carboxylate-($COO^-$) and/or sulfonate-($SO_3^-$), $m_1$, $m_2$, $m_3$ are the same or different whole numbers from 0 to 3, at least one of $m_1$, $m_2$ or $m_3$ being equal to or greater than 1; $n_1$, $n_2$, $n_3$ are the same or different whole numbers from 0 to 5, M is an alkali metal, an equivalent of an alkaline earth metal or zinc, ammonium or quaternary ammonium of the formula $N(R^3R^4R^5R^6)^+$, where $R^3$, $R^4$, $R^5$, $R^6$ individually are a straight-chain or branched alkyl of 1 to 18 carbon atoms or an aralkyl of 7 to 14 carbon atoms. Quaternary ammonium groups where three of the $R^3$, $R^4$, $R^5$, $R^6$ each contain 1 to 4 carbon atoms and the fourth group is an aralkyl of 7 to 14 carbon atoms have proved particularly useful.

Water-soluble triarylphosphines of the formula described above are preferred wherein $Ar^1$, $Ar^2$, $Ar^3$ are phenyl and $X^1$, $X^2$, $X^3$ are sulfonate or a carboxylate. Examples of compounds of the formula described above are triphenylphosphine trisodium trisulfonate, triphenylphosphine tri(tetraalkylammonium) trisulfonate, triphenylphosphine trisodium tricarboxylate.

The sulfonated or carboxylated arylphosphines can be used as single compounds. However, phosphine mixtures containing different numbers of sulfonate or carboxylate groups can also be used, i.e. mixtures of salts of triarylphosphine trisulfonic acids and triarylphosphine disulfonic acids. Moreover, the sulfonates or carboxylates need not contain the same cation. Mixtures of salts derived from different metals and/or containing ammonium and/or quaternary alkylammonium ions are suitable.

The catalyst system consisting of a rhodium complex compound and excess water-soluble phosphines is used as an aqueous solution generally containing 50 to 800 wt. ppm of rhodium and 25 to 30 wt. % of water-soluble phosphine, in each case based on the solution. It has proved particularly useful to work with solutions containing 200 to 600 wt. ppm of rhodium and 26 to 28 wt. % of water-soluble phosphine.

A particular advantage of the catalyst system described above is that it is highly selective towards the formation of n-aldehyde which is in most cases more valuable for further use, while iso-aldehyde for example is only formed to a very minor extent. Thus, when propylene is hydroformylated, 95 wt. % of n-butyraldehyde is formed and only 5% of the iso compound.

When the same catalyst solution is used continuously or repeatedly, the selective effect of the catalyst system diminishes over the course of time. Although the reaction conditions remain the same, the amount of n-aldehyde per unit of rhodium and per time unit falls in favor of the formation of iso-aldehyde. One cause of this loss of selectivity is the transformation of water-soluble phosphines into compounds which are no longer capable of forming complexes with rhodium. Thus, the P-C bonds between the phosphorus atom and the phenyl or naphthyl group containing sulfonate or carboxylate groups are broken by hydrolysis or phosphorus (V) compounds are formed by oxidation. Apart from other unidentified substances, salts of aromatic sulfonic acids and disulfophenylphosphinic acid have been found as transformation products of salts of triphenylphosphine sulfonic acids. These reactions cause the ratio of phosphine molecules to rhodium atoms to fall thus reducing the selectivity of the catalyst system.

As the cost of effectiveness of the catalyst processes greatly depends in many cases on the life of the catalysts, great efforts have been made to maintain the activity of the catalyst and its selectivity at the same high level over as long a period as possible.

OBJECTS OF THE INVENTION

It is an object of the invention to provide an improved hydroformylation process which either avoids or at least minimizes the drop in selectivity of the catalyst system due to transformation of the water-soluble phosphines.

This and other objects and advantages of the invention will become obvious from the following detailed description.

THE INVENTION

The novel hydroformylation process for the preparation of aldehydes by reacting aliphatic olefins of 2 to 12 carbon atoms with carbon monoxide and hydrogen at temperatures of 20° to 150° C. and pressures of 0.1 to 20 mPa in the liquid phase and in the presence of an aqueous solution containing 50 to 800 wt. ppm of rhodium and 25 to 30 wt. % of phosphines, in each case based on the aqueous solution as a catalyst system and in addition transformation products of the phosphines, characterized in that part of the aqueous solution of the catalyst system is drawn off together with the reaction product and replaced by fresh solution. Continual replacement of part of the solution of the catalyst system ensures that the concentration of the transformation products does not exceed a certain limit.

Surprisingly, it has been found that, as the concentration of the transformation products increases, their rate of formation in the catalyst solution rises sharply and the transformation products may well promote their own formation from the water-soluble phosphines so that one may speak of a kind of autocatalyst process. However, it is also possible that as the solution is deprived of phosphorus ligands, rhodium complex compounds dissociate and rhodium atoms form clusters with the formation of metal-metal bonds which clusters catalytically accelerate the formation of phosphine transformation products. This behavior causes the phosphine concentration to decrease disproportionately and not linearly over the course of time.

Small amounts of transformation products in the catalyst system are not detrimental. It is not possible to say generally what amounts are tolerable as this is an individual matter and depends on the reaction conditions and the olefinic compounds used, among other factors. The decisive factor for the use of the process of the invention is the increase of the iso compound in the reaction mixture compared with the proportion of iso-aldehyde. The term "transformation products" in the sense of the present invention is understood to be all the phosphorus compounds which form from the water-soluble phosphines during the hydroformylating reaction and which do not form complex compounds with rhodium.

In the new process, the aqueous solution of the catalyst system can be treated continuously in which part of the catalyst solution is removed from the reaction mixture together with the reaction product and replaced by fresh solution. However, it is also possible to remove some of the solution discontinuously from time to time and replace it by fresh solution.

The catalyst can be added to the reaction mixture in a preformed state, i.e. as a rhodium complex compound containing phosphine and carbon monoxide. However, the components of the rhodium complex compound can also be added just as successfully by dosing the rhodium as a water-soluble rhodium salt such as rhodium sulfate, rhodium acetate, rhodium-2-ethylhexanoate and the carboxylated or sulfonated triphenyl or trinaphthylphosphine, e.g. as a sodium salt. Both complexing components can also be introduced separately as solutions. The complex compound is then formed under the conditions of the hydroformylation reaction and with the assistance of the carbon monoxide contained in the synthesis gas. The concentration of rhodium and phosphine in the fresh solution generally coincides with the concentration of these components in the catalyst solution, and is thus around 50 to 800 wt. ppm of rhodium and 25 to 30 wt. % of phosphine.

The separated catalyst solution is worked up to recover the rhodium complex compound and excess water-soluble phosphines by known processes. A suitable work-up process is, for example, the extraction of the previously acidified solution with the solution of an amine in an organic solvent and subsequent treatment of the organic phase with the aqueous solution of an inorganic base. According to another procedure, the rhodium complex compound and phosphines including their transformation products are separated by a membrane separation process. The rhodium complex compound can be used immediately again as a catalyst component while the phosphine is recovered by extraction with amine.

According to the process described in the invention, olefins of 2 to 12 carbon atoms can be hydroformylated and these olefins can be linear or branched and contain a terminal or internal double bond. Cycloolefins of 6 to 12 carbon atoms can also be reacted. Examples of the olefins are ethylene, propylene, 1-butene, 2-butene, 1-pentene, 2-methyl-1-butene, 4,4-dimethyl-1-nonene, 1-dodecene, cyclohexene, dicyclopentadiene. It is preferred to use linear olefins of 2 to 8 carbon atoms such as ethylene, propylene, 1-butene, 1-pentene, 1-hexene, 1-heptene and 1-octene or in the case of cycloolefins, dicyclopentadiene.

The total pressure of hydrogen and carbon monoxide amounts to 0.1 to 20 mPa, preferably 1 to 10 mPa. The composition of the synthesis gas, i.e. the ratio of carbon monoxide to hydrogen can be varied within wide limits and generally synthesis gas is added in which the volume ratio of carbon monoxide to hydrogen is 1:1 or only deviates slightly from this value. The reaction takes place at temperatures of 20° to 150° C. and it can be carried out continuously or batchwise.

In the following examples there are described several preferred embodiments to illustrate the invention. However, it should be understood that the invention is not intended to be limited to the specific embodiments.

EXAMPLE 1 (comparative Example)

Propylene, carbon monoxide and hydrogen in a volume ratio of 1:1:1 in an aqueous catalyst solution containing 26 wt. % of a mixture of the sodium salts of triphenylphosphine trisulfonic acid and triphenylphosphine disulfonic acid and 450 wt. ppm of rhodium are reacted at a temperature of 125° C. and a pressure of 5 mPa to obtain 2.1 moles of a mixture of 95% n and 5% isobutyraldehyde per liter of catalyst solution and per hour. In the course of time, the proportion of iso-aldehyde in the reaction product increased constantly i.e. the selectivity of the reaction fell.

EXAMPLE 2

Example 1 was repeated with the only difference being that when the selectivity of the reaction fell, indicated by an increase of the proportion of iso-aldehyde in the reaction product from 5 to 7 wt. %, 10 wt. % of the catalyst solution was removed and replaced by the same amount of fresh solution (with 26 wt % of a mixture of the sodium salts of triphenylphosphine trisulfonic acid and triphenylphosphine disulfonic acid and 450 wt. ppm of rhodium as acetate). In this manner, it was possible to re-establish the original selectivity of the reaction. The catalyst removed was worked up, e.g. by extraction, to recover the rhodium and phosphine. The procedure can be repeated as often as desired so that the course of the reaction is maintained constant over a long period.

Various modification of the process of the invention may be made without departing from the spirit or scope thereof and it is to be understood that the invention is intended to be limited only as defined in the appended claims.

What we claim is:

1. In a hydroformylation process for the preparation of aldehydes by reacting aliphatic olefins of 2 to 12 carbon atoms with carbon monoxide and hydrogen at temperatures of 20° to 150° C. and pressures of 0.1 to 20 mPa in the liquid phase and in the presence of an aqueous solution containing 50 to 800 wt. ppm of rhodium and 25 to 30 wt. % of phosphines, in each case based on the aqueous solution as a catalyst system and in addition the transformation products of the phosphines, the improvement comprising draining off a portion of the aqueous solution of the catalyst system together with the reaction product and replacing the same with fresh aqueous solution of the catalyst system.

2. The process of claim 1 wherein the fresh solution contains rhodium as a water-soluble salt and water-soluble phosphine and that the catalyst system is formed in the hydroformylation zone.

* * * * *